(12) United States Patent
Greatbatch et al.

(10) Patent No.: US 6,988,001 B2
(45) Date of Patent: Jan. 17, 2006

(54) HERMETIC COMPONENT HOUSING FOR PHOTONIC CATHETER

(75) Inventors: Wilson Greatbatch, Akron, NY (US); Michael L. Weiner, Webster, NY (US)

(73) Assignee: Biophan Technologies, Inc., West Henrietta, NY (US)

( * ) Notice: Subject to any disclaimer, the term of this patent is extended or adjusted under 35 U.S.C. 154(b) by 478 days.

(21) Appl. No.: 10/283,530

(22) Filed: Oct. 30, 2002

(65) Prior Publication Data

US 2003/0083728 A1    May 1, 2003

Related U.S. Application Data

(60) Provisional application No. 60/334,704, filed on Oct. 31, 2001.

(51) Int. Cl.
*A61N 1/362* (2006.01)

(52) U.S. Cl. .............................................. 607/9; 607/37

(58) Field of Classification Search .............. 607/9–26, 607/36, 37
See application file for complete search history.

(56) References Cited

U.S. PATENT DOCUMENTS

| | | |
|---|---|---|
| 3,057,356 A | 10/1962 | Greatbatch |
| 3,478,746 A | 11/1969 | Greatbatch |
| 3,508,167 A | 4/1970 | Russell, Jr. |
| 3,669,095 A | 6/1972 | Kobayashi et al. |
| 3,686,958 A | 8/1972 | Porter et al. |
| 3,718,142 A | 2/1973 | Mulier |
| 3,789,667 A | 2/1974 | Porter et al. |
| 3,825,015 A | 7/1974 | Berkovits |
| 4,012,641 A | 3/1977 | Brickerd, Jr. et al. |
| 4,041,954 A | 8/1977 | Ohara |
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |

(Continued)

FOREIGN PATENT DOCUMENTS

WO    WO 01/74241    10/2001

OTHER PUBLICATIONS

A. Jerwzewski et al.;, "Development of an MRI-Compatible Catheter for Pacing the Heart: Initial In Vitro and in Vivo Results," JMRI, ISHRM (US), vol. 6 (No. 6), p. 948-949, (Jun. 14, 1996).

(Continued)

*Primary Examiner*—Scott M. Getzow

(57) ABSTRACT

A hermetic component housing for use with a photonic catheter connected to a photonic pacemaker or other medical system designed for compatibility with Magnetic Resonance Imaging (MRI) procedures. The hermetic housing includes a housing body having a proximal end and a distal end. The body is formed with a hermetically sealed interior for carrying one or more electrical and/or optical components therein. The proximal end of the body is adapted to mount to a distal end of a photonic catheter carrying a fiber optic element or bundle. A hermetic terminal is provided to allow the fiber optic element or bundle to communicate with the body interior. The body can be adapted to mount (or function as) one or more electrodes designed for delivering or sensing electrical signals to body tissue, or it may be adapted to mount no electrodes. The component housing may be implemented by itself at the distal end of the photonic catheter, or it may be used in conjunction with other housings of like or different construction.

39 Claims, 9 Drawing Sheets

U.S. PATENT DOCUMENTS

| | | | |
|---|---|---|---|
| 4,254,776 A | 3/1981 | Tanie et al. |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,545,381 A | 10/1985 | Bournay, Jr. et al. |
| 4,611,127 A | 9/1986 | Ibrahim et al. |
| 4,677,471 A | 6/1987 | Takamura et al. |
| 4,686,964 A | 8/1987 | Yunoki et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | deLaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,454,837 A * | 10/1995 | Lindegren et al. ............. 607/9 |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,679,026 A | 10/1997 | Fain et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,755,742 A | 5/1998 | Schuelke et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,861,012 A | 1/1999 | Stroebel |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,897,577 A | 4/1999 | Cinbis et al. |
| 5,899,927 A | 5/1999 | Ecker et al. |
| 5,902,326 A | 5/1999 | Lessar et al. |
| 5,916,162 A | 6/1999 | Snelton et al. |

| | | |
|---|---|---|
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Alled, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,129,745 A | 10/2000 | Sun et al. |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,317,633 B1 | 11/2001 | Jorgenson et al. |
| 6,367,984 B1 | 4/2002 | Stephenson et al. |
| 6,416,510 B1 | 7/2002 | Altman et al. |
| 2002/0138124 A1 | 9/2002 | Helfer et al. |

OTHER PUBLICATIONS

W. Moshage et al., "A Non-Magnetic, MRI Compatible Pacing Center for Clinical Application in Magnetocardiography," Biomedizinixche Technik Band, Erganzungsband (Germany), p. 162-163, (Jun. 14, 1990).

C. Roos, et al.,"Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85-94.

Mark B. M. Hofman;"MRI-Compatible Cardiac Pacing Catheter," JMRI; May/Jun. 1997; p. 612.

A.A. Damji et al., "RF Interference Suppression in a Cardiac Synchronization System Operating in High Magnetic Field NMR Imaging System," Magnetic Resonance Imaging, vol. 6, pp 637-640, (1988).

Frank G. Shellock et al., "Burns Associated with the use of Monitoring Equipment during MR Procedures," JMRI, Jan./Feb. 1996; pp. 271-272.

J. Nyenhuis et al., "Heating Near Implanted Medical Devices by the MRI RF-Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1998, vol. 8 #6; pp. 1338-1342.

J. Rod Gimbel et al., "Safe Performance of Magnetic Resonance," PACE; vol. 19; Jun. 1996; pp. 913-919.

National Library of Medicine; "Rapid Ventricular Pacing in a Pacemaker Patient Undergoing Magnetic Resonance Imaging," Pub Med; Pacing Clin Electrophysiol; Jun. 1998; p. 1.

National Library of Medicine;"Effects of Magnetic Resonance Imaging on Cardiac Pacemakers and Electrodes, " Pub Med; Am Heart J; (1997); pp. 1-2.

M. Kusumoto et al., "Cardiac Pacing for the Clinician," Lippincott Williams & Wilkins; (2001); Chapter 1, pp. 9, 12, 13, 18, 22, 24.

Donald Fink; "Electronic Engineering," Electronic Engineers Handbook; 2nd edition, Mcgraw Hill; (1982); Section 14; pp. 29-45.

X Luo et al., "Electromagnetic Interference Shielding Using Continuous Carbon-Fiber Carbon-Matrix and Polymer-Matrix Composites," Composites Part B: Engineering; (1999); pp. 227-231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p 161-163.

M. Konings et al., "Catheters and Guidewires in Inerventional MRI; Problems and Solutions," Medical Mundi; 45/1; Mar. (2001).

M. Konings; "Development of an MR-Safe Tracking Catheter with a Laser Driven Tip Coil," Journal of Magnetic Resonance Imaging 2001:13:131-135. c. 2001 Wiley-Liss, Inc.

Ey Yong et al., "An Optical System for Wireless Detuning of Parallel Resonant Circuits" Journal of Magnetic Resonance Imaging; (2000); vol. 12, pp. 632-638.

Bernd Nowak; "Taking Advantage of Sophisticated Pacemaker Diagnostics," Excerpta Medica; (1999); pp. 172D-179D.

Jose A. Jogler et al., "Interaction of a Commercial Heart Rate Monitor With Implanted Pacemakers," Excerpta Medica; (1999); pp. 790-792.

J.A. Pomposo et al., "Polypyrrole-based Conducting Hot Melt Adhesives for EMI Shielding Applications," Elsevier; Synthetic Metals 104; (1999); pp. 107-111.

K. Grattan et al., "Fiber Optic Sensor Technology: An Overview," Elsevier; Sensors and Actuators 82; (2000);pp. 40-61.

L. Rippert et al., "Optical and Acoustic Damage Detection in Laminated CFRP Composite Materials," Elsevier; Composites Science and Technology 60; (2000); pp. 2713-2724.

C. Strandman et al., "A Production Process of Silicon Sensor Elements for a Fibre-Optic Pressure Sensor," Elsevier; Sensors and Actuators A63; (1997); pp. 69-74.

D. Howard et al., "A Single-Fringe Etalon Silicon Pressure Transducer," Elsevier; Sensors and Actuators 86; (2000); pp. 21-25.

Dan Haronian, "Displacement Sensing Using Geometrical Modulation in Reflection Mode (GM-RM) of Coupled Optical Waveguides," J. Micromech, Microeng., (UK), (1998); pp. 323-326.

H Ghafouri-Shiraz, "A Novel Distributed Feedback Laser Diode Structure foran Optical Wavelength Tunable Filter," Semicond. Sci. Technol. 12; (UK), (1997); pp. 1161-1165.

L. Kasarian, "A New Optical Fiber Multiplexer for Distortion-Free Light Transfer in Multichannel Fiber Optic Sensor Systems," Elsevier; Sensors and Actuators 84; (2000); pp. 250-258.

X. Yan et al., "Electric Field Controlled 2×2 Bypass Exchange Photorefractive Switch," IOP Publishing; (UK) (1998), pp. 383-386.

E. Piener et al., "A Micromachined Vibration Sensor Based on the Control of Power Transmitted Between Optical Fibres," Elsevier; Sensors and Actuators A65; (1998) pp. 23-29.

D. Sun et al., "High Performance Unidirectional Electrooptic Modulator Based On Polymeric Highly Multi-Mode Waveguides,"Elsevier; Optics & Laser Technology 30; (1998); 481-489.

Engin Molva; "Microchip Lasers and Their Applications in Optical Microsystems," Elsevier; Optical Materials 11; (1999); pp. 289-299.

J. Linares et al., "Theory and Design of an Integrated Optical Sensor Based on Planar Waveguiding Lenses," Elsevier; Optics Communications 180; (2000); pp. 29-36.

O. Parriaux et al., "Coupling Gratings as Waveguide Functional Elements," IOP Publishing; Pure Appl. Opt. 5; (1996); pp. 453-469.

E T Enikov et al., "Three-Dimensional Microfabrication for a Multi- Degree of Freedom Capacitive Force Sensor Using Fibre-Chip Coupling" IOP Publishing; (UK); J. Micromechl. Microeng. 10;(2000) pp. 492-497.

J. Holm et al., "Through-Etched Silicon Carriers for Passive Alighnment of Optical Fibers to Surface-Active Optoelectronic Components" Elsevier;Sensors and Actuators 82; (2000) pp. 245-248.

M. Kimura et al., "Vibration Sensor Using Optical-Fiber Catilever with Bulb-Lens" Elsevier; Sensors and Actuators A66; (2000) pp. 178-183.

Y. Mao et al., "Three-Stage Wavelength Converter Based on Cross-Grain Modulation in Semiconductor Optical Amplifiers"Elsevier; Optics Communications 167; (1999) pp. 57-66.

X. Hu et al., "Dynamically Induced Irreversibility: Light Amplification and Quantum Noise Reduction in a V-Type Three-Level System" IOP Publishing; J. Opt. B: Quantum Semiclass. Opt. 2; (UK) (2000): pp. 570-575.

Y. Yim et al., "Lithium Niobate Integrated-Optic Voltage Sensorwith Variable Sensing Ranges" Elsevier; Optics Communications 152; Jul. 1, 1998; pp. 225-228.

C. Lee et al., "Electromagnetic Interference Shilding Efficiency of Polyaniline Mixtures and Multilayer Films" Elsevier; Synthetic Metals 102; (1999) pp. 1346-1349.

Marc Desmulliez, "Optoelectronics-VLSI System Integration Technological Challenges" Elsevier; Materials Science and Engineering B74;(2000) pp. 269-275.

J. Zook et al., "Fiber-optic Vibration Sensor Baed on Frequency Modulation of Light-Excited Oscillators" Elsevier; Sensors and Actuators 83; (2000); pp. 270-276.

M. Reta-Hernandez et al., "Attenuation of Low Frequency Magnetic Fields Using Active Shielding" Elsevier; Electronic Power Systems Research 45; (1998); pp. 57-63.

C. Huang et al., "The EMI Shielding Effectiveness of PC/ABS/Nickel-Coated Carbon-Fibre Composites" Elsevier: European Polymer Journal 36; (2000) pp. 2727-2737.

M. Balucani et al., "Optical Link for Digital Transmissions Using Porou Silicon Light Emitting Diode" Elsevier; Journal of Non-Crystalline Solids 266-269; (2000) pp. 1238-1240.

D. Egelman et al., "Calcium Dynamics in the Extracellular Space of Mammalian Nerual Tissue" Biophysical Jourmal; vol. 76; Apr. 1999; pp. 1856-1867.

* cited by examiner

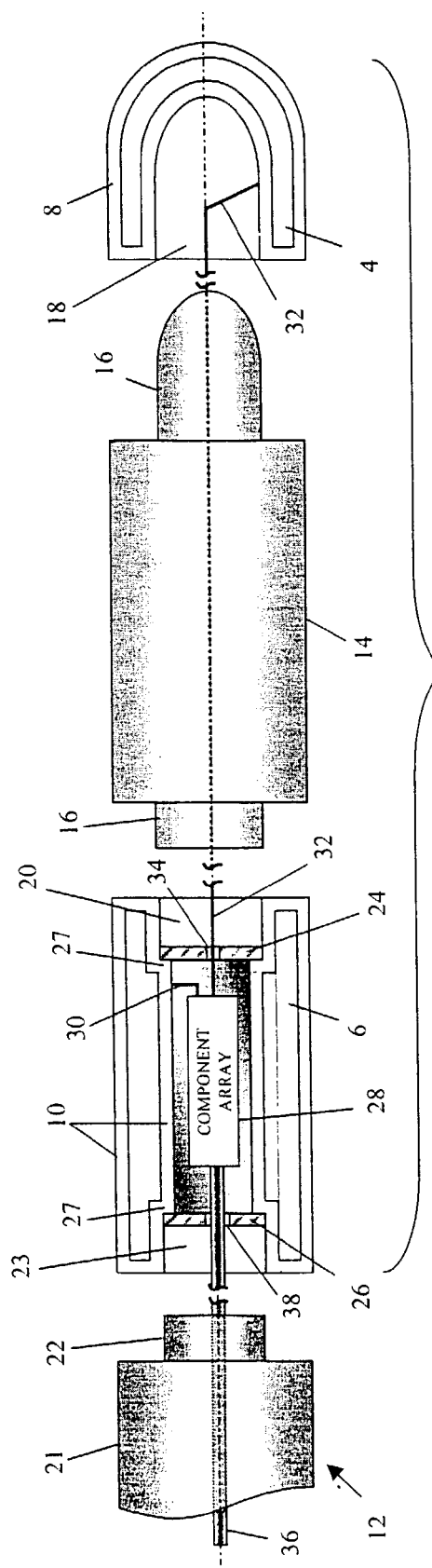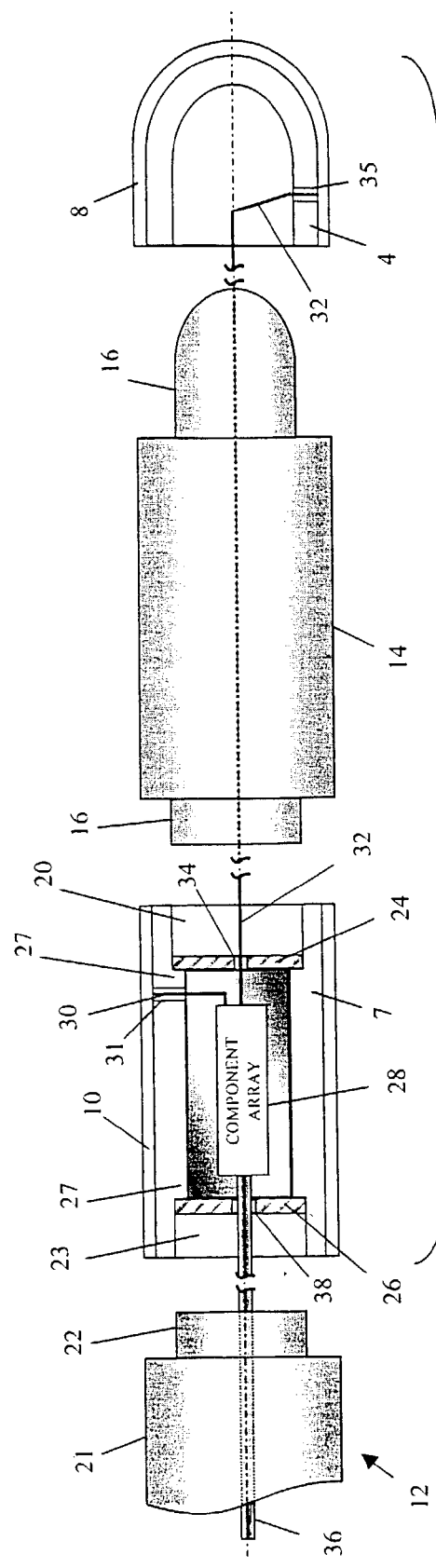
FIG. 2B
FIG. 2C

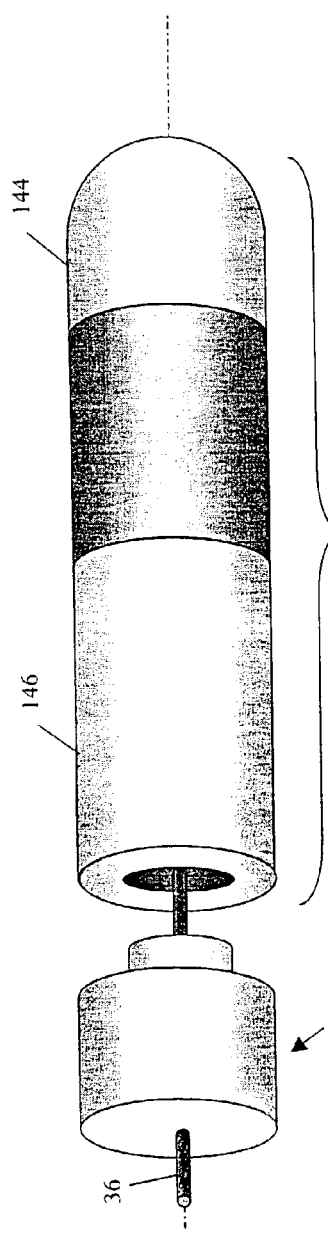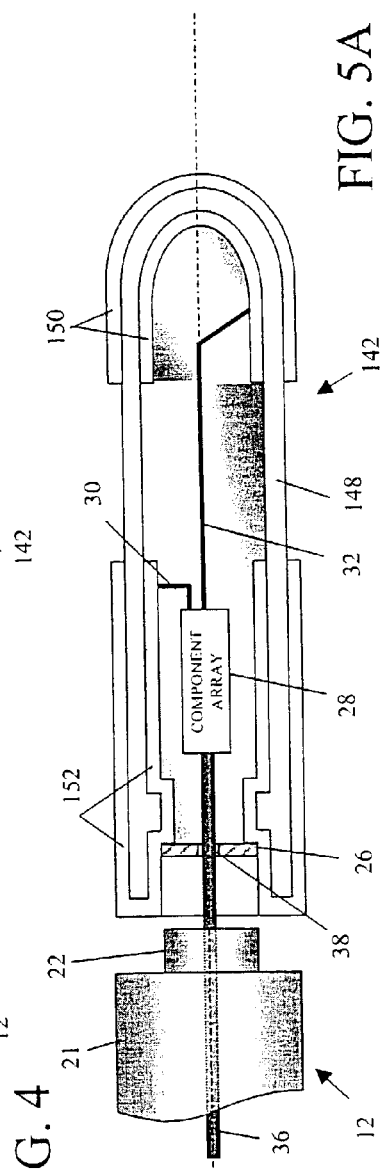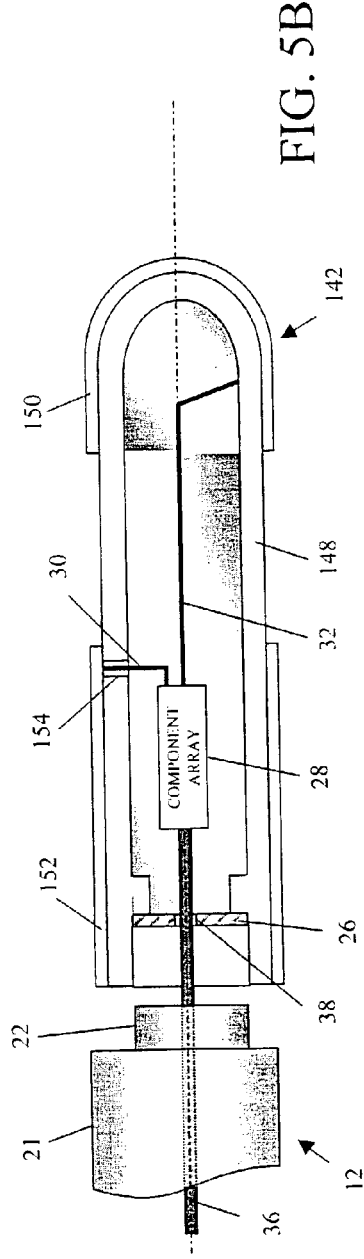

HERMETIC COMPONENT HOUSING FOR PHOTONIC CATHETER

PRIORITY INFORMATION

The present patent application claims priority under 35 U.S.C. §119 from U.S. Provisional Patent Application Ser. No. 60/334,704 filed on Oct. 31, 2001. The entire contents of U.S. Provisional Patent Application Ser. No. 60/334,704, filed on Oct. 31, 2001, are hereby incorporated by reference.

FIELD OF THE PRESENT INVENTION

The present invention relates to photonic pacemakers and other photonic medical systems. More particularly, the invention concerns photonic catheter component housings and electrode systems designed for compatibility with MRI diagnostic apparatus.

BACKGROUND OF THE PRESENT INVENTION

The metallic cardiac electrodes and leads used in conventional cardiac stimulation and monitoring devices have always been a problem. They tend to fatigue, corrode, and break. Their physical properties (corrosion, strength, chemical activity, etc.) limit the materials which can be used to titanium, platinum metals, their alloys, to certain stainless steels, and to special structures to limit fatigue (such as spring coils, metal cladding, multiple strands, etc.) With respect to metallic leads, a leaky interface is often produced between the metal and the insulating sheath that surrounds the leads.

The problem of metallic leads has been addressed by applicants' assignee in an effort to provide a pacemaker that is compatible with MRI diagnostic imaging procedures. See copending Ser. Nos. 09/864,944 and 09/865,049, both filed on May 24, 2001, and copending Ser. Nos. 09/885,867 and 09/885,868, both filed on Jun. 20, 2001. In these copending patent applications, the contents of which are fully incorporated herein by this reference, MRI compatible/safe pacemakers are disclosed for both implantable and wearable service. The disclosed pacemakers feature photonic catheters carrying optical signals in lieu of metallic leads carrying electrical signals in order to avoid the dangers associated with MRI-generated electromagnetic fields. Electro-optical and opto-electrical conversion systems are disposed at the proximal and distal ends of the photonic catheters to perform the necessary conversions between electrical and optical signaling modes.

The devices of the copending applications require component housings at the each end of the photonic catheter to house the conversion systems and other components. This not a problem at the proximal end because the main pacemaker enclosure is situated at that location. At the distal end, a micro-miniature housing is required that is preferably no wider than the diameter of the photonic catheter, such that catheter insertion is not hampered. In addition to being small in size, the distal component housing must be hermetically sealed to protect the components therein from patient body fluids. Moreover, it should preferably carry at least one of the electrodes used for cardiac stimulation and/or sensing. It is thus purpose and goal of the present invention to address alternative designs for hermetic component housings designed for implantable service at the distal end of a photonic catheter in a photonic pacemaker system.

The foregoing problems are solved by a hermetic component carrying housing for use with a photonic catheter connected to a photonic pacemaker or other medical system designed for compatibility with Magnetic Resonance Imaging (MRI) procedures. The hermetic housing includes a housing body having a proximal end and a distal end. The body is formed with a hermetically sealed interior for carrying one or more electrical and/or optical components therein. The proximal end of the body is adapted to mount to a distal end of a photonic catheter carrying a fiber optic element or bundle. A hermetic terminal is provided to allow the fiber optic element or bundle to communicate with the body interior. The body can be adapted to mount one or more electrodes designed for delivering or sensing electrical signals to body tissue, or it may be adapted to mount no electrodes. The component housing may be implemented by itself at the distal end of the photonic catheter, or it may be used in conjunction with other housings of like or different construction.

SUMMARY OF THE PRESENT INVENTION

A first aspect of the present invention is a hermetic housing for mounting to a distal end of a photonic catheter and adapted to house an optical component therein. The hermetic housing includes a housing body having a proximal end and a distal end; a hermetically sealed interior in the housing body for enclosing the optical component therein, the proximal end of the housing body being adapted to mount to a distal end of a photonic catheter having a fiber optic element; and a hermetic terminal allowing the fiber optic element to communicate with the housing body interior.

A second aspect of the present invention is a hermetic component carrying housing in a photonic pacemaker. The hermetic component carrying housing includes a housing body having a proximal end and a distal end; a hermetically sealed interior in the housing body enclosing an optical component therein, the proximal end of said housing body being mounted to a distal end of a photonic catheter carrying a fiber optic element; and a hermetic terminal allowing the fiber optic element to communicate with the housing body interior.

A third aspect of the present invention is a medical system. The medical system includes a control unit adapted to generate body tissue stimulation signals; a photonic catheter having a proximal end in communication with the control unit and a fiber optic element for carrying optical stimulation signals, the catheter further having a distal end; and a hermetic housing. The hermetic housing includes a housing body having a proximal end and a distal end, a hermetically sealed interior in the housing body enclosing an optical component therein, the proximal end of the housing body being mounted to the distal end of the photonic catheter, a hermetic terminal allowing the photonic catheter fiber optic element to communicate with the housing body interior, and means for delivering the stimulation signals to implanted body tissue.

A fourth aspect of the present invention is a medical system. The medical system includes a control unit adapted to receive sensing signals representing one or more body function parameters; a photonic catheter having a proximal end in communication with the control unit and a fiber optic element for carrying optical sensing signals, the catheter further having a distal end; and a hermetic housing. The hermetic housing includes a housing body having a proximal end and a distal end, a hermetically sealed interior in the housing body enclosing an optical component therein, the proximal end of the housing body being mounted to the distal end of the photonic catheter, a hermetic terminal allowing the photonic catheter fiber optic element to communicate with the housing body interior, and means for sensing body function parameters and generating the sensing signals.

A fifth aspect of the present invention is a photonic catheter unit adapted for use with a medical system. The photonic catheter unit includes a hermetic component carrying housing; a fiber optic element for carrying optical stimulation signals between a control unit located at a proximal end of fiber optic element and the hermetic component carrying housing located at a distal end of said fiber optic element; and a biocompatible sheath covering the fiber optic element. The hermetic component carrying housing includes a housing body having a proximal end and a distal end, a hermetically sealed interior in the housing body enclosing an optical component therein, the proximal end of the housing body being mounted to the distal end of fiber optic element, a hermetic terminal allowing the photonic catheter fiber optic element to communicate with the housing body interior, and means for delivering the stimulation signals to implanted body tissue.

A sixth aspect of the present invention is a photonic catheter unit adapted for use with a medical system. The photonic catheter unit includes a hermetic component carrying housing; a fiber optic element for carrying optical sensing signals between a control unit located at a proximal end of fiber optic element and the hermetic component carrying housing located at a distal end of the fiber optic element; and a biocompatible sheath covering the fiber optic element. The hermetic component carrying housing includes a housing body having a proximal end and a distal end, a hermetically sealed interior in the housing body, enclosing an optical component therein, the proximal end of the housing body being mounted to the distal end of fiber optic element, a hermetic terminal allowing the photonic catheter fiber optic element to communicate with the housing body interior, and means for sensing one or more body function parameters and generating the sensing signals.

BRIEF DESCRIPTION OF THE DRAWINGS

The foregoing and other features and advantages of the invention will be apparent from the following more particular description of preferred embodiments of the invention, as illustrated in the accompanying Drawing in which:

FIGS. 2A, 2B and 2C are sectional axial centerline views showing alternative ways in which the component housing of FIG. 1 can be configured to provide photonic pacemaker electrode terminations;

FIG. 4 is a partially exploded perspective view of a hermetic component housing constructed in accordance with another embodiment of the present invention;

FIGS. 5A and 5B are sectional axial centerline views showing alternative ways in which the component housing of FIG. 4 can be configured to provide photonic pacemaker electrode terminations;

DETAILED DESCRIPTION OF THE PREFERRED EMBODIMENTS OF THE PRESENT INVENTION

Figure 1:
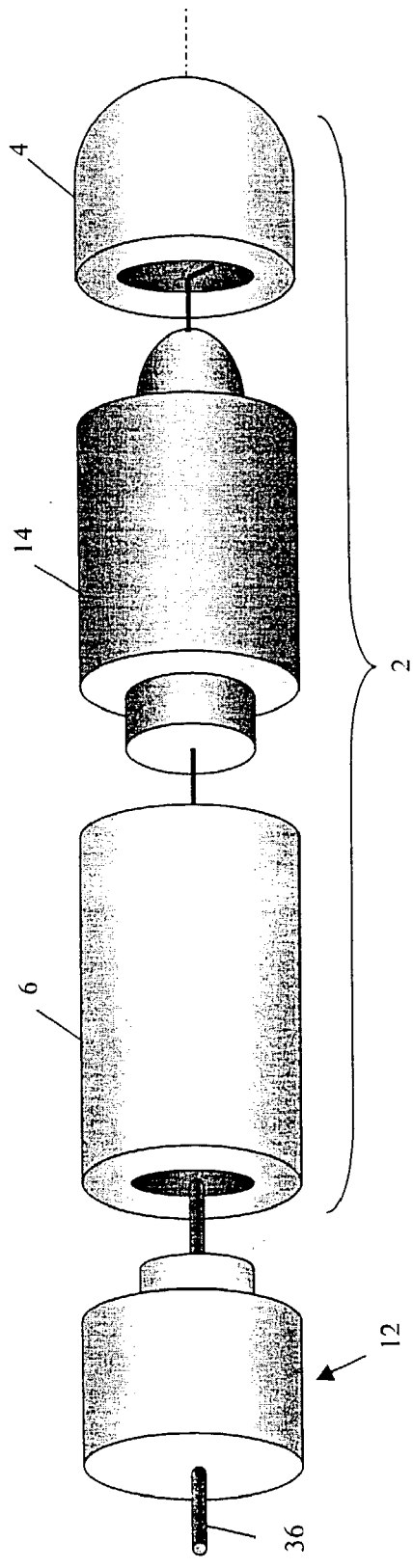
FIG. 1 is an exploded perspective view of a hermetic component housing constructed in accordance with one embodiment of the present invention.

Turning now to FIG. 1, a first embodiment of the invention is shown in which a hermetic housing is constructed to provide part of an electrode termination pair 2. The electrode termination pair 2 includes a cup-shaped structure (tip) 4 acting as a tip electrode and the hermetic housing 6 (ring) acting as a ring electrode. The tip 4 and the ring 6 are both substantially cylindrical in shape, and preferably have the same wall thickness. Note that the tip 4 has a rounded nose portion and a base portion that is planar in cross-section. The ring 6 has proximal and distal end portions that are both preferably planar in cross section.

Figure 2A:
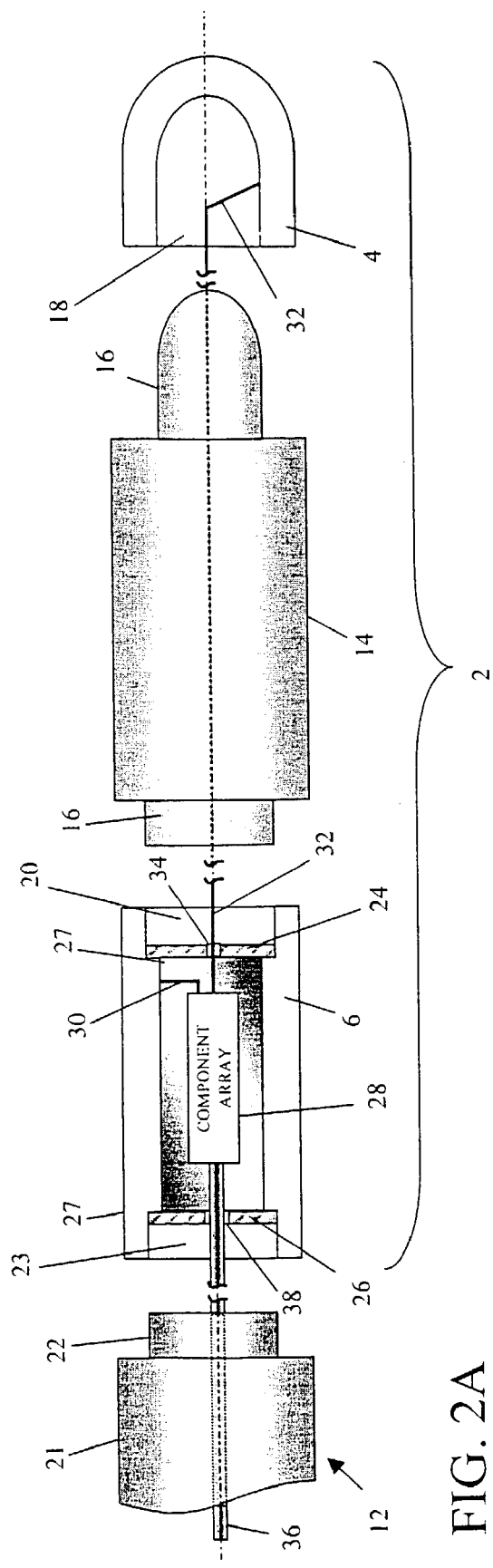

As shown in FIG. 2A, the tip 4 and the ring 6 can be made from a biocompatible, non-ferromagnetic metal such as platinum, titanium or alloy of platinum or titanium. As shown in FIGS. 2B and 2C, the tip 4 and the ring 6 can be made of a non-metallic material, such as ceramic, and covered with electrically conductive coatings 8 and 10, respectively. The difference between FIGS. 2B and 2C is that all exposed surfaces of the tip 4 and the ring 6 are coated in FIG. 2B, whereas only the outer surface of the tip and ring are coated in FIG. 2C.

If a ceramic is used to form the tip 4 and the ring 6, the material used is preferably a suitable biocompatible ceramic material such a ceramic of the type commonly used for joint prostheses. By way of example only, such material is available from Ceramic Components Inc. of Latrobe, Pa. To form a ceramic tip and ring, a ceramic slurry can be formed into the desired shapes and fired to bake the ceramic material.

The electrically conductive coatings 8 and 10 are preferably formed by very thinly coating the tip 4 and the ring 6, as by electroplating, sputtering or other deposition technique, etc., with a suitable metal. To facilitate MRI compatibility, the metal preferably has low magnetic susceptibility, such as titanium, platinum, an alloy of titanium or platinum, or the like. Preferably, the coatings 8 and 10 are applied as thin as possible to achieve the twin goals of efficient electrical interaction with implanted tissue while minimizing interaction with MRI induced electromagnetic fields. By way of example, the thickness of the coatings 8 and 10 may range from mono-molecular thickness to sub-micron or micron level thickness.

FIGS. 1, 2A, 2B and 2C show the electrode termination pair 2 of FIG. 1 being mounted to the distal end of a photonic catheter 12 of the type disclosed in the co-pending applications referenced above. The tip 4 and the ring 6 are also interconnected by a short insulative stub 14 that is solid, generally cylindrical in shape, and made from silicone, polyurethane, polyethylene, or any other suitable biocompatible electrically insulating material. The outside diameter of the stub 14 preferably equals the outside diameter of the tip 4 and the ring 6, to facilitate efficient implantation and removal in a patient. The ends of the stub 14 can be bonded to the tip 4 and the ring 6 using a suitable medical adhesive. To provide additional connection integrity, the stub 14 can be formed with end portions 16 of reduced diameter. One end portion 16 of the stub 14 is received into an opening 18 in the base portion of the tip 4 and bonded therein. The other end portion 16 of the stub 14 is received into an opening 20 in the distal end of the ring 6 and bonded therein.

The completed tip/ring assembly can be mounted to the distal end of the photonic catheter 12 in similar fashion. In particular, the photonic catheter 12 will be a generally cylindrical element whose exterior sheath 21 is made from silicone, polyurethane, polyethylene, or any other suitable biocompatible electrically insulating material. Note that the sheath 21 could be tubular in shape, with a small center bore carrying one or more optical conductors therein. Alternatively, the sheath 21 could be formed around the optical conductors such that the conductors are embedded in the material of the sheath. In either case, the outside diameter of the sheath 21 will preferably be the same as that of the ring 6 and can be bonded thereto using a suitable medical adhesive. To provide additional connection integrity, the sheath 21 may be formed with a small end portion 22 of reduced diameter that is snugly received within an opening 23 in the proximal end the ring 6 and bonded therein.

Because the ring 6 functions as a hermetically sealed component housing, it must be provided with hermetically sealed closures at or near the ends thereof. These closures may be provided by a pair of closure walls 24 and 26 that are secured within the interior of the ring 6. The closure walls 24 and 26 can be formed from any suitable biocompatible material capable of sealing the ring interior, including metals, polymers, and potentially other materials. To facilitate the secure hermetic attachment of the closure walls 24 and 26, the inside of the ring 6 can be formed with a pair of recessed annular shoulders 27.

There may be disposed within the ring 6 any number of components for delivering electrical signals to, or sensing biological activity in, a body. Such components are collectively shown as a component array by reference numeral 28, and may include opto-electrical transducers, electro-optical transducers, signal processors and amplifiers, digital microprocessors, temperature sensors, R-wave sensors, partial oxygen sensors, and any number of other components. To provide electrical interaction with surrounding body tissue, a positive terminal of the component array 28 is connected to a short metallic lead 30 made from copper or other suitable material of low magnetic susceptance.

In FIG. 2A, the lead 30 is electrically connected to the ring 6 by attaching it, as by soldering or the like, directly to the ring itself. In FIG. 2B, the metallic lead 30 is electrically connected to the ring 6 by attaching it, as by soldering or the like, to an interior portion of the metallic coating 10. In FIG. 2B, the metallic lead 30 is fed through a small hole 31 in the wall of the ring 6 so that it may be attached to the exterior metallic coating 10, as by soldering or the like. A negative terminal of the component array 28 connects to a longer metallic lead 32 that is also made from copper or other suitable material of low magnetic susceptance. This metallic lead 32 feeds through a hermetic seal terminal 34 mounted on the closure wall 24. It then extends through the material of the stub 14 (which can be molded around the lead 32) and into the tip 4. In FIG. 2A, the metallic lead is electrically attached, as by soldering or the like, directly to the tip itself. In FIG. 2B, the metallic lead 32 is electrically attached, as by soldering or the like, to an interior portion of the metallic coating 8. In FIG. 2C, the metallic lead 32 is fed through a small hole 35 in the ceramic wall of the tip 4 so that it may be attached to the metallic coating 8, as by soldering or the like.

When the tip 4 and the ring 6 are implanted in a patient's heart, the tip 4 will typically be embedded in the endocardial tissue, while the ring 6 is situated in the right ventricle, in electrical contact with the endocardium via the ventricular blood. If the photonic catheter 12 is connected to a pacemaker, an optical pulse emanating from a photonic pacemaker pulsing unit (not shown) is sent down a fiber optic element or bundle 36 of the photonic catheter 12. The fiber optic element or bundle 36 passes into the hermetically sealed interior of the ring 6 via a hermetic seal terminal 38. There, the fiber optic element or bundle 36 delivers the optical pulse to the component array 28, which preferably includes a photodiode array. The photodiode array produces an electrical impulse that negatively drive the tip 4 with respect to the ring 6 at a potential of about 3–4 volts and a current level of about 3 milliamperes for a total power output of about 10 milliwatts. Note that a sensing function could be added by incorporating an electro-optical transducer into the component array 28. Electrical sense signals would then be converted to optical signals and placed on the fiber optic element or bundle 36 for delivery to a sensing unit (not shown).

Figure 3:
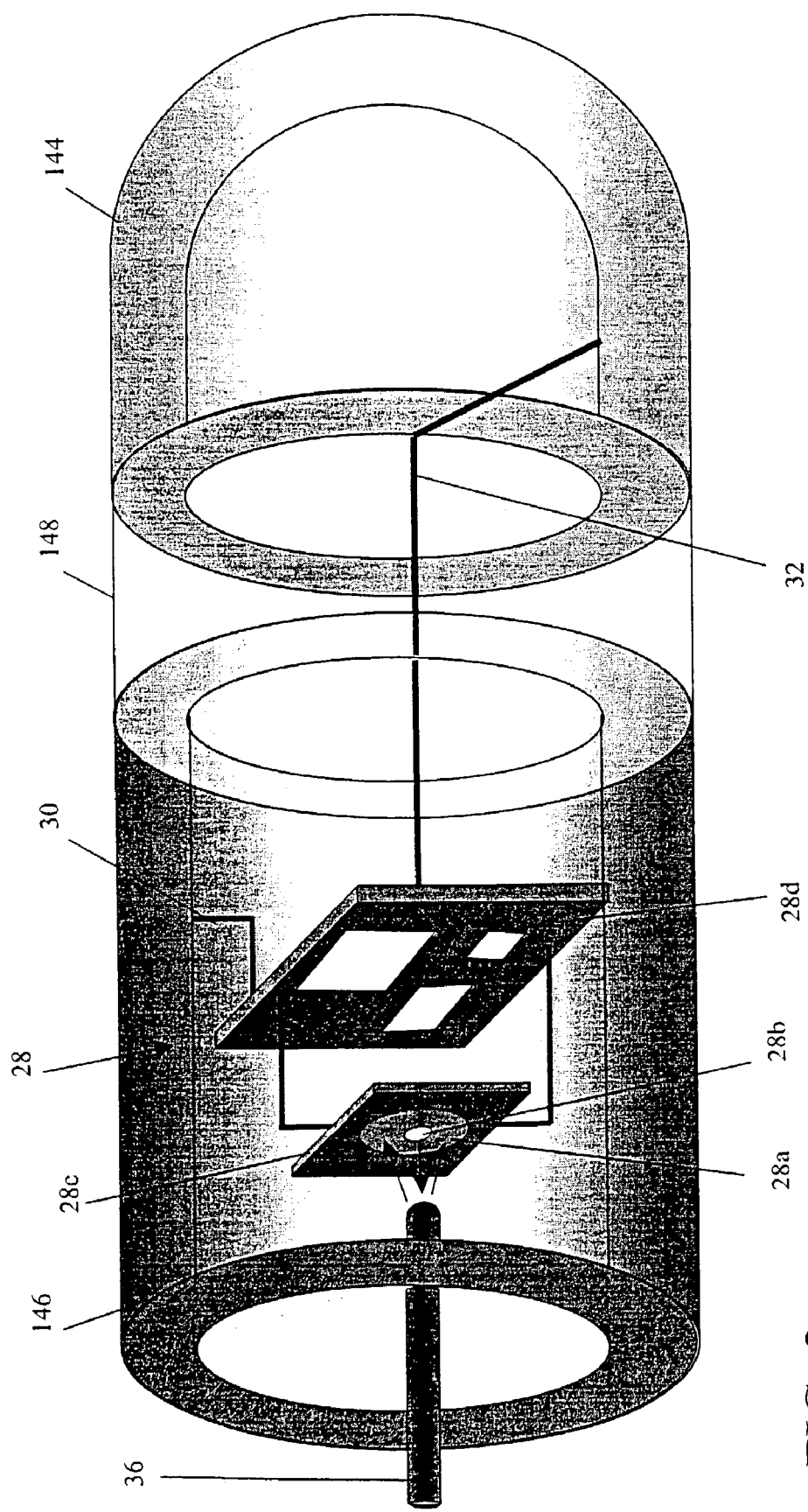
FIG. 3 is a perspective view of the component housing of FIG. 1 showing details of exemplary components that may be housed therein.

FIG. 3 illustrates an exemplary construction of the component array 28 in which the array comprises a photodiode array 28a for receiving optical pacing signals from the fiber optic element or bundle 36 and a light emitting diode 28b for delivering optical sensing signals to the fiber optic element or bundle 36. The components 28a and 28b are mounted on a circuit substrate 28c that is electrically connected to an electrical circuit unit 28d, that may include amplifiers, oscillators, a microprocessor and other devices that can assist electrical pulse delivery and biological sensing functions.

Turning now to FIG. 4, another embodiment of the invention is shown in which a modified hermetic housing provides a complete electrode termination pair 142. The electrode termination pair 142 includes a tip 144 and a ring 146 that are constructed as metallic coatings formed on the hermetic housing, which is designated by reference numeral 148. An electrically conductive coating 150 formed at the distal end of the housing 148 provides the tip 144. An electrically conductive coating 152 formed at the proximal end of the housing 148 provides the ring 146. The difference between FIGS. 5A and 5B is that both the inside and the outside surfaces of the housing 148 are coated in FIG. 5A, whereas only the outer surface of the housing 148 is coated in FIG. 5B.

FIGS. 5A and 5B also show that the component array 28 of FIGS. 1–3 can be hermetically sealed within the housing 148 via the hermetic seal 26. The proximal end of the housing 148 may then be secured to the distal end of the photonic catheter 12, and the fiber optic element or array 36 can be connected to the component array 28 via the hermetic terminal 38. The component array 28 is electrically connected to the tip 144 and the ring 146 via the electrical leads 32 and 30, respectively.

Figure 6:
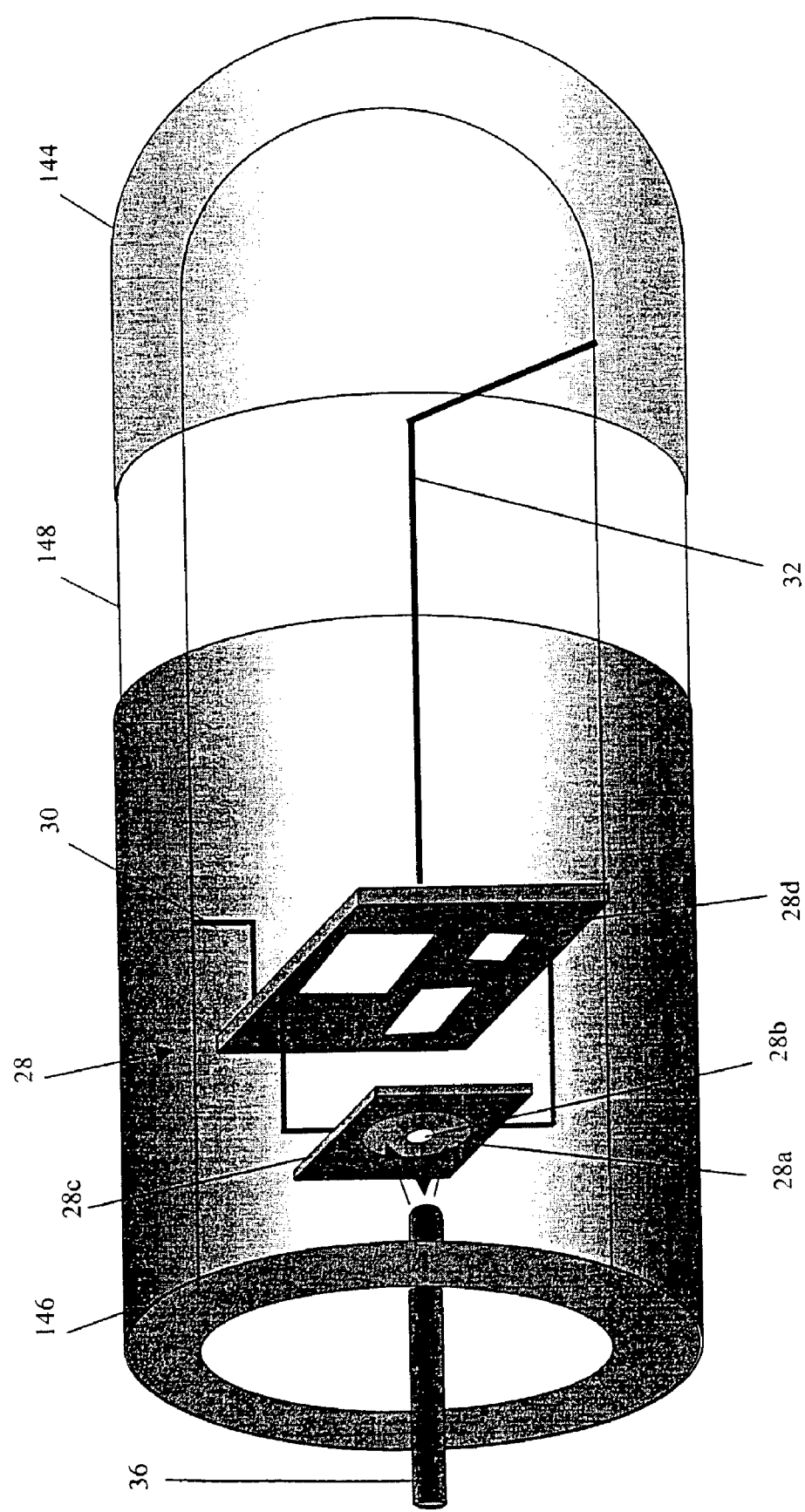
FIG. 6 is a perspective view of the component housing of FIG. 4 showing details of exemplary components that may be housed therein.

FIG. 6 shows an exemplary implementation of the component array 28 within the housing 148. This component array configuration is identical to the component array configuration of FIG. 4, and the description thereof will not be repeated here.

Figure 7:
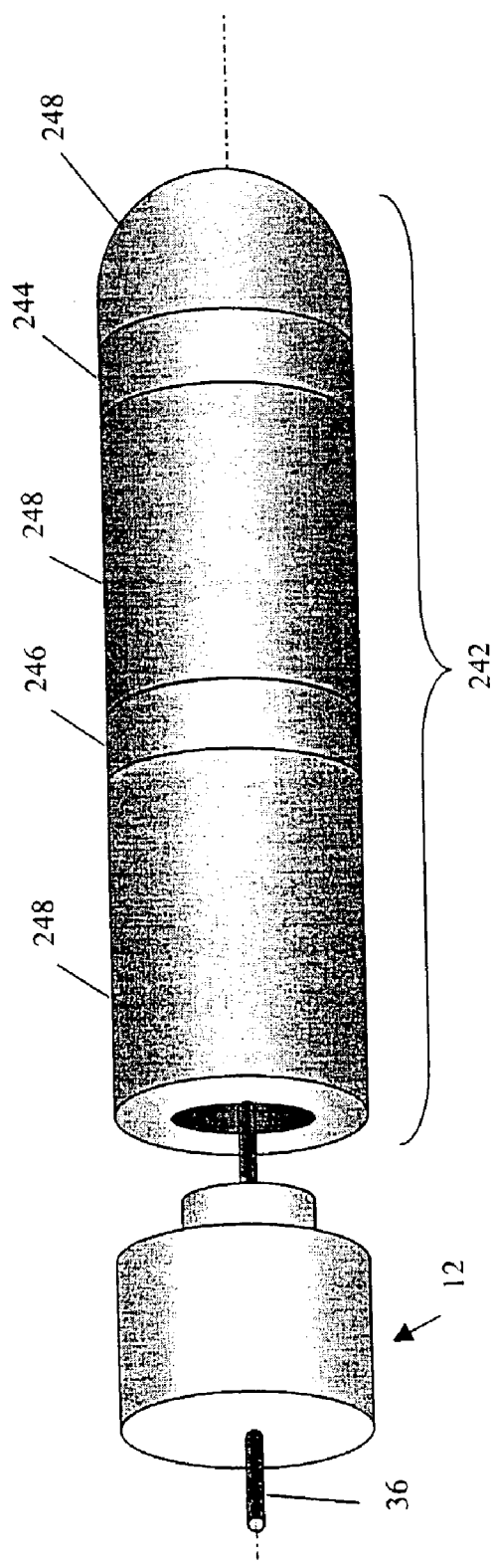
FIG. 7 is a partially exploded perspective view of a hermetic component housing constructed in accordance with another embodiment of the present invention.

Turning now to FIG. 7, another embodiment of the invention is shown in which a modified hermetic housing again provides a complete electrode termination pair 242. The electrode termination pair 242 includes a tip electrode 244 and a ring electrode 246 that are constructed as electrically conductive band coatings on the hermetic housing, which is designated by reference numeral 248. A shallow well 250 formed near the distal end of the housing 248 may be used to mount the tip 244. A shallow well 252 formed toward the proximal end of the housing 248 may be used to mount the ring 246.

Figure 8:
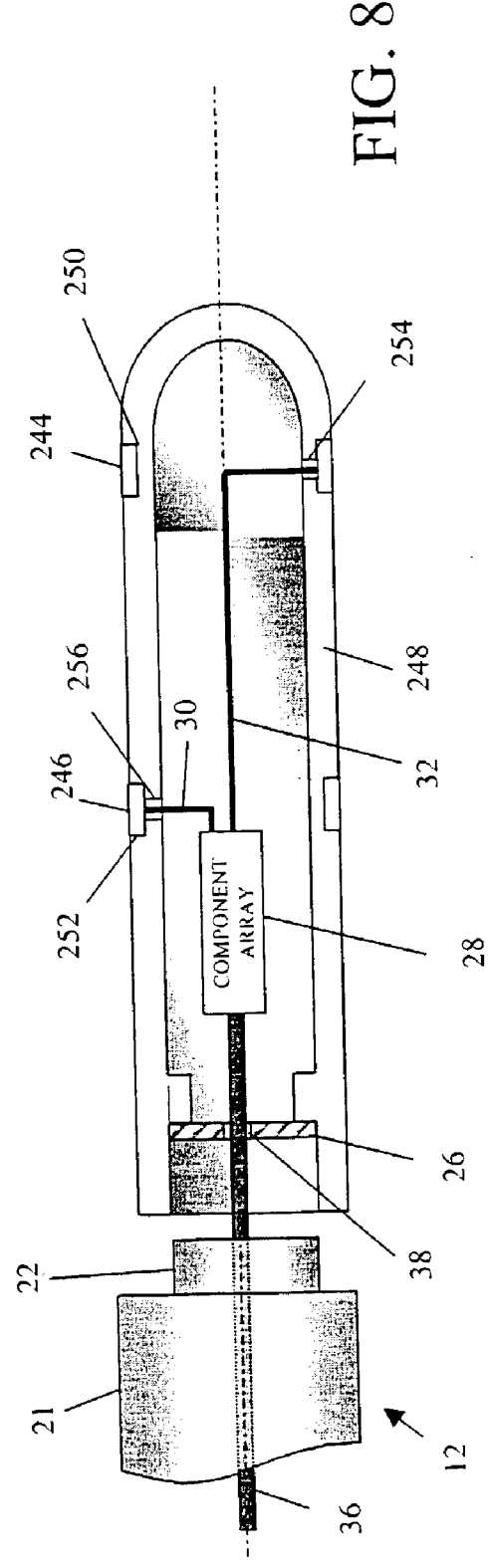
FIG. 8 is a sectional view taken along the axial centerline of the component housing of FIG. 7.

FIG. 8 also shows that the component array 28 of FIGS. 1–3 can be hermetically sealed within the housing 248 via the hermetic seal 26. The proximal end of the housing 248 may then be secured to the distal end of the photonic catheter 12, and the fiber optic element or array 36 can be connected to the component array 28 via the hermetic terminal 38. The component array 28 is electrically connected to the tip 244 and the ring 246 via the electrical leads 32 and 30, respectively. Note that the lead 32 feeds through a small hole 254 formed in the housing 248 in order to reach the tip 244. Similarly, the lead 30 feeds through a small hole 256 formed in the housing 248 in order to reach the ring 246.

Figure 9:
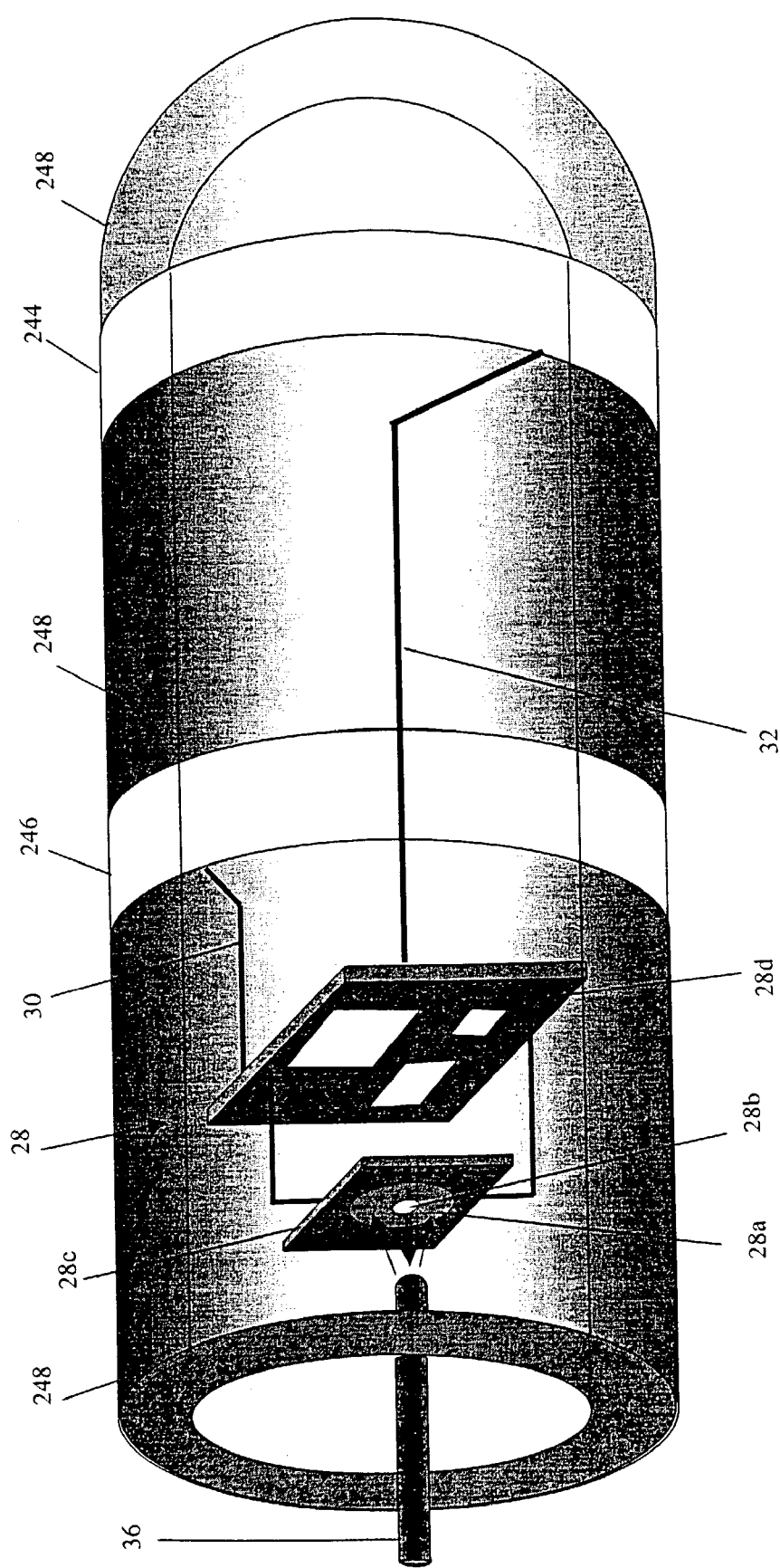
FIG. 9 is a perspective view of the component housing of FIG. 7 showing details of exemplary components that may be housed therein.

FIG. 9 shows an exemplary implementation of the component array 28 within the housing 248. This component array configuration is identical to the component array configuration of FIG. 4, and the description thereof will not be repeated here.

Figure 10:
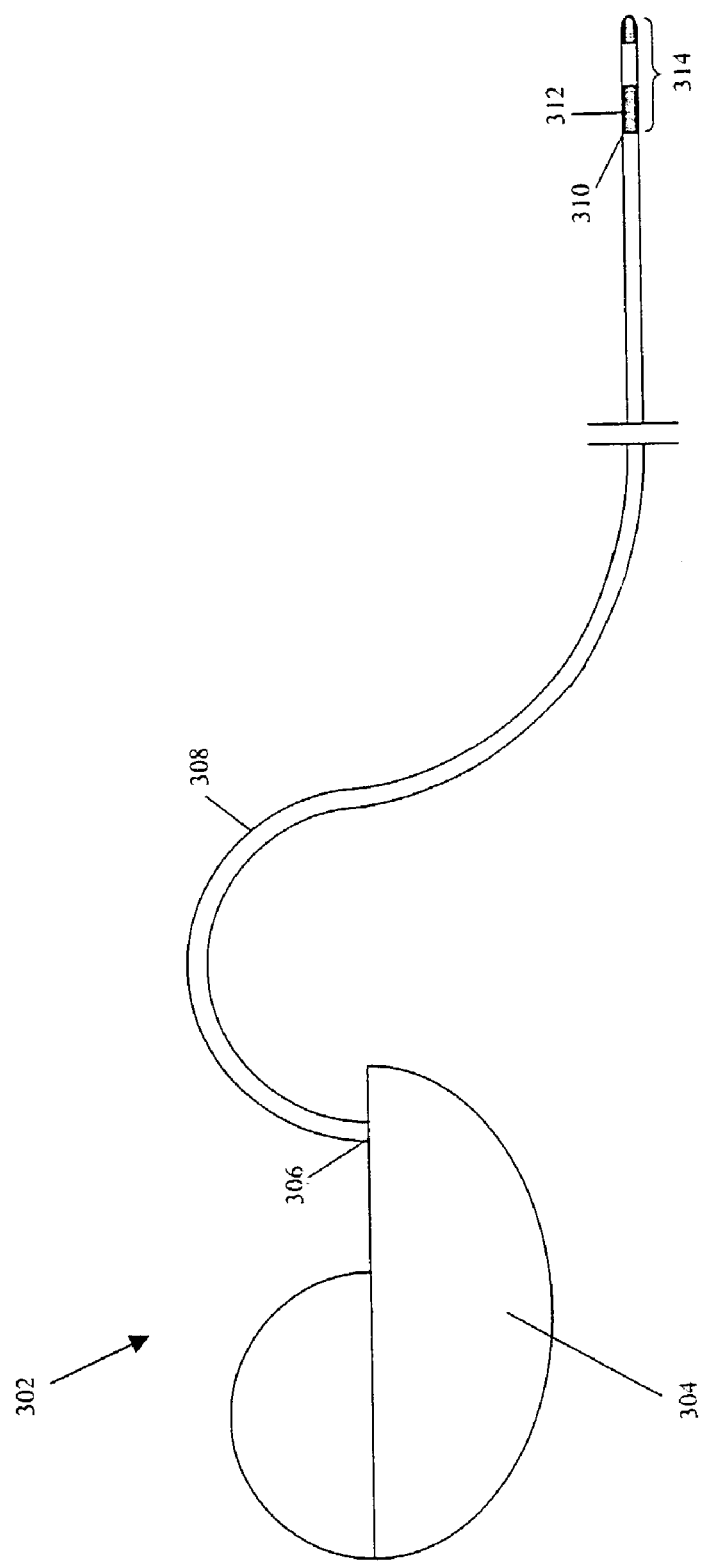
FIG. 10 is a diagrammatic view of an implantable pacemaker comprising a hermetic housing in accordance with the invention.

Turning now to FIG. 10, an implantable pacemaker 302 is shown that may be constructed in accordance with the present invention. The pacemaker 302 includes a first (main) enclosure 304 that is connected to the proximal end 306 of a photonic catheter 308. A distal end 310 of the photonic catheter 308 mounts a hermetic housing 312 constructed in accordance with a suitable one of the embodiments disclosed herein. As also described above, the housing 312 can form all or part of a tip/ring electrode termination pair 314, and will house a component array 28 containing suitable electrical and optical components to perform whatever pacing and/or sensing functions are required.

Figure 11:
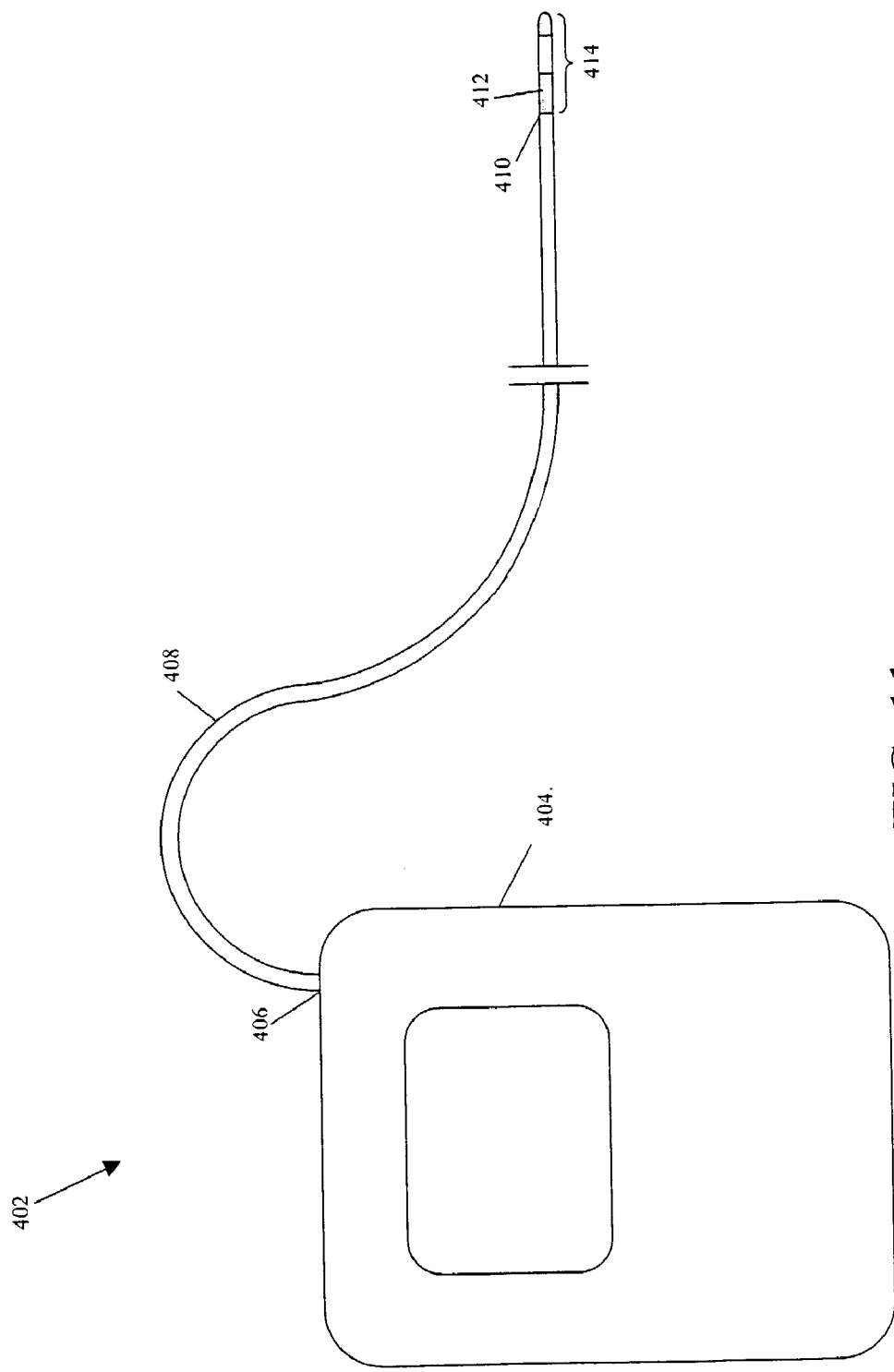
FIG. 11 is a diagrammatic view of a wearable pacemaker comprising a hermetic housing in accordance with the invention.

Turning now to FIG. 11, a wearable pacemaker 402 is shown that may be constructed in accordance with the present invention. The pacemaker 402 includes a first (main) enclosure 404 that is connected to the proximal end 406 of a photonic catheter 408. A distal end 410 of the photonic catheter 408 mounts a hermetic housing 412 constructed in accordance with a suitable one of the embodiments disclosed herein. As also described above, the housing 412 can form all or part of a tip/ring electrode termination pair 414, and will house a component array 28 containing suitable electrical and optical components to perform whatever pacing and/or sensing functions are required.

While various embodiments of the present invention have been shown and described, it should be apparent that many variations and alternative embodiments could be implemented in accordance with the invention. For example, although only a single hermetic housing is shown being attached to the distal end of a photonic catheter, a chain of several hermetic housings can be used, each containing one or more electrical and/or optical components for performing one or more biologically useful functions relative to an implanted patient. In addition, although the hermetic housings are shown to be adapted to mount, or to function as, an electrode or an electrode pair, the housings could be implemented without electrodes thereon in device implementations where there are other structures that mount, or function as, electrodes.

It is understood, therefore, that the present invention is not to be in any way limited except in accordance with the spirit of the appended claims and their equivalents.

What is claimed is:

1. A hermetic housing for mounting to a distal end of a photonic catheter and adapted to house an optical component therein, comprising:
   a housing body having a proximal end and a distal end;
   a hermetically sealed interior in said housing body for enclosing the optical component therein;
   said proximal end of said housing body being adapted to mount to a distal end of a photonic catheter having a fiber optic element; and
   a hermetic terminal allowing said fiber optic element to communicate with said housing body interior;
   said housing body being made from an electrically conductive material of low magnetic susceptance.

2. The hermetic housing as claimed in claim 1, wherein said hermetically sealed interior in said housing body encloses an electrical component therein.

3. The hermetic housing as claimed in claim 1, wherein said fiber optic element is part of a fiber optic bundle.

4. The hermetic housing as claimed in claim 1, wherein said housing body interior houses an opto-electrical transducer in the form of a photodiode array.

5. The hermetic housing as claimed in claim 4, wherein said housing body interior houses an electro-optical transducer in the form of a light emitting diode and a sense signal amplifier.

6. The hermetic housing as claimed in claim 5, wherein said housing body interior houses a microprocessor.

7. The hermetic housing as claimed in claim 6, wherein said housing body interior houses components for sensing one or more of core body temperature, cardiac R waves, and partial oxygen pressure.

8. A hermetic housing for mounting to a distal end of a photonic catheter and adapted to house an optical component therein, comprising:
   a housing body having a proximal end and a distal end;
   a hermetically sealed interior in said housing body for enclosing the optical component therein;
   said proximal end of said housing body being adapted to mount to a distal end of a photonic catheter having a fiber optic element; and
   a hermetic terminal allowing said fiber optic element to communicate with said housing body interior;
   said housing body being made from a non-electrically conductive material and having a coating layer comprising an electrically conductive material of low magnetic susceptance to allow said hermetic housing to function as a ring electrode.

9. The hermetic housing as claimed in claim 8, wherein said distal end of said housing is adapted to mount to a proximal end of an insulative stub carrying a tip electrode structure, and wherein said housing includes a second hermetic terminal allowing an electrical lead to extend from said housing body interior through said stub to said tip electrode structure.

10. The hermetic housing as claimed in claim 9, wherein said housing body is made from a ceramic material and said tip and said ring coatings are metallic coatings selected from the group comprising platinum, titanium, and alloys thereof.

11. The hermetic housing as claimed in claim 8, wherein said housing body is made from a ceramic material and said tip and said ring coatings are metallic coatings selected from the group comprising platinum, titanium, and alloys thereof.

12. A hermetic housing for mounting to a distal end of a photonic catheter and adapted to house an optical component therein, comprising:
a housing body having a proximal end and a distal end;
a hermetically sealed interior in said housing body for enclosing the optical component therein;
said proximal end of said housing body being adapted to mount to a distal end of a photonic catheter having a fiber optic element; and
a hermetic terminal allowing said fiber optic element to communicate with said housing body interior;
said housing body being made from a non-electrically conductive material and has having a pair of spaced coating layers comprising an electrically conductive material of low magnetic susceptance to allow said hermetic housing to function as a combination tip and ring electrode.

13. The hermetic housing as claimed in claim 12, wherein said housing body is made from a ceramic material and said tip and said ring coatings are metallic coatings selected from the group comprising platinum, titanium, and alloys thereof.

14. In a photonic pacemaker, a hermetic component carrying housing, comprising:
a housing body having a proximal end and a distal end;
a hermetically sealed interior in said housing body enclosing an optical component therein;
said proximal end of said housing body being mounted to a distal end of a photonic catheter carrying a fiber optic element; and
a hermetic terminal allowing said fiber optic element to communicate with said housing body interior;
said housing body being made from an electrically conductive material of low magnetic susceptance.

15. The hermetic component carrying housing as claimed in claim 14, wherein said hermetically sealed interior in said housing body encloses an electrical component therein.

16. The hermetic component carrying housing as claimed in claim 14, wherein said fiber optic element is part of a fiber optic bundle.

17. The hermetic component carrying housing as claimed in claim 14, wherein said housing body interior houses an opto-electrical transducer in the form of a photodiode array.

18. The hermetic component carrying housing as claimed in claim 17, wherein said housing body interior houses an electro-optical transducer in the form of a light emitting diode and a sense signal amplifier.

19. The hermetic component carrying housing as claimed in claim 18, wherein said housing body interior houses a microprocessor.

20. The hermetic component carrying housing as claimed in claim 19, wherein said housing body interior houses components for sensing one or more of core body temperature, cardiac R waves, and partial oxygen pressure.

21. In a photonic pacemaker, a hermetic component carrying housing, comprising:
a housing body having a proximal end and a distal end;
a hermetically sealed interior in said housing body enclosing an optical component therein;
said proximal end of said housing body being mounted to a distal end of a photonic catheter carrying a fiber optic element; and
a hermetic terminal allowing said fiber optic element to communicate with said housing body interior;
said housing body being made from a non-electrically conductive material and having a coating layer comprising an electrically conductive material of low magnetic susceptance to allow said hermetic housing to function as a ring electrode.

22. The hermetic component carrying housing as claimed in claim 21, wherein said distal end of said housing is mounted to a proximal end of an insulative stub carrying a tip electrode structure, and wherein said housing includes a second hermetic terminal allowing an electrical lead to extend from said housing body interior through said stub to said tip electrode structure.

23. The hermetic component carrying housing as claimed in claim 22, wherein said housing body is made from a ceramic material and said tip and said ring coatings are metallic coatings selected from the group consisting of platinum, titanium and alloys thereof.

24. In a photonic pacemaker, a hermetic component carrying housing, comprising:
a housing body having a proximal end and a distal end;
a hermetically sealed interior in said housing body enclosing an optical component therein;
said proximal end of said housing body being mounted to a distal end of a photonic catheter carrying a fiber optic element; and
a hermetic terminal allowing said fiber optic element to communicate with said housing body interior;
said housing body being made from a non-electrically conductive material and having a pair of spaced coating layers comprising an electrically conductive material of low magnetic susceptance to allow said hermetic housing to function as a combination tip and ring electrode.

25. The hermetic component carrying housing as claimed in claim 24, wherein said housing body is made from a ceramic material and said tip and said ring coatings are metallic coatings selected from the group consisting of platinum, titanium and alloys thereof.

26. A medical system, comprising:
a control unit adapted to generate body tissue stimulation signals;
a photonic catheter having a proximal end in communication with said control unit and a fiber optic element for carrying optical stimulation signals, said catheter further having a distal end; and
a hermetic housing;
said hermetic housing including,
a housing body having a proximal end and a distal end,
a hermetically sealed interior in said housing body inclosing an optical component therein,
said proximal end of said housing body being mounted to said distal end of said photonic catheter,
a hermetic terminal allowing said photonic catheter fiber optic element to communicate with said housing body interior, and means for delivering said stimulation signals to implanted body tissue.

27. The medical system as claimed in claim 26, wherein said hermetically sealed interior in said housing body encloses an electrical component therein.

28. The medical system as claimed in claim 26, wherein said fiber optic element is part of a fiber optic bundle.

29. The medical system as claimed in claim 26, wherein said control unit is adapted to receive sensing signals representing one or more body function parameters and said means senses body function parameters and generates said sensing signals.

30. A medical system, comprising:
a control unit adapted to receive sensing signals representing one or more body function parameters;

a photonic catheter having a proximal end in communication with said control unit and a fiber optic element for carrying optical sensing signals, said catheter further having a distal end; and a hermetic housing;

said hermetic housing including,
- a housing body having a proximal end and a distal end,
- a hermetically sealed interior in said housing body enclosing an optical component therein,
- said proximal end of said housing body being mounted to said distal end of said photonic catheter,
- a hermetic terminal allowing said photonic catheter fiber optic element to communicate with said housing body interior, and
- means for sensing body function parameters and generating said sensing signals.

31. The medical system as claimed in claim 30, wherein said hermetically sealed interior in said housing body encloses an electrical component therein.

32. The medical system as claimed in claim 30, wherein said fiber optic element is part of a fiber optic bundle.

33. A photonic catheter unit adapted for use with a medical system, comprising:

a hermetic component carrying housing;

a fiber optic element for carrying optical stimulation signals between a control unit located at a proximal end of fiber optic element and said hermetic component carrying housing located at a distal end of said fiber optic element; and a biocompatible sheath covering said fiber optic element;

said hermetic component carrying housing including,
- a housing body having a proximal end and a distal end,
- a hermetically sealed interior in said housing body enclosing an optical component therein,
- said proximal end of said housing body being mounted to said distal end of fiber optic element,
- a hermetic terminal allowing said photonic catheter fiber optic element to communicate with said housing body interior, and
- means for delivering said stimulation signals to implanted body tissue.

34. The photonic catheter unit as claimed in claim 33, wherein said hermetically sealed interior in said housing body encloses an electrical component therein.

35. The photonic catheter unit as claimed in claim 33, wherein said fiber optic element is part of a fiber optic bundle.

36. The photonic catheter unit as claimed in claim 33, wherein said fiber optic element carries optical sensing signals between the control unit located at the proximal end of fiber optic element and said hermetic component carrying housing located at the distal end of said fiber optic element and said means senses body function parameters and generates said sensing signals.

37. A photonic catheter unit adapted for use with a medical system, comprising:

a hermetic component carrying housing;

a fiber optic element for carrying optical sensing signals between a control unit located at a proximal end of fiber optic element and said hermetic component carrying housing located at a distal end of said fiber optic element; and a biocompatible sheath covering said fiber optic element;

said hermetic component carrying housing including,
- a housing body having a proximal end and a distal end,
- a hermetically sealed interior in said housing body enclosing an optical component therein,
- said proximal end of said housing body being mounted to said distal end of fiber optic element,
- a hermetic terminal allowing said photonic catheter fiber optic element to communicate with said housing body interior, and
- means for sensing one or more body function parameters and generating said sensing signals.

38. The photonic catheter unit as claimed in claim 37, wherein said hermetically sealed interior in said housing body encloses an electrical component therein.

39. The photonic catheter unit as claimed in claim 37, wherein said fiber optic element is part of a fiber optic bundle.

* * * * *